US008460339B2

(12) United States Patent
Anderson

(10) Patent No.: US 8,460,339 B2
(45) Date of Patent: *Jun. 11, 2013

(54) MULTI ELEMENT BIASED SUTURE CLIP

(75) Inventor: Steven C. Anderson, Mountain View, CA (US)

(73) Assignee: Abbott Laboratories, Abbott Park, IL (US)

(*) Notice: Subject to any disclaimer, the term of this patent is extended or adjusted under 35 U.S.C. 154(b) by 181 days.

This patent is subject to a terminal disclaimer.

(21) Appl. No.: 12/869,014

(22) Filed: Aug. 26, 2010

(65) Prior Publication Data
US 2010/0324598 A1 Dec. 23, 2010

Related U.S. Application Data

(63) Continuation of application No. 11/461,323, filed on Jul. 31, 2006, now Pat. No. 7,806,910, which is a continuation of application No. 10/305,923, filed on Nov. 26, 2002, now Pat. No. 7,108,710.

(51) Int. Cl.
*A61B 17/04* (2006.01)

(52) U.S. Cl.
USPC ............. 606/232; 606/74; 24/67.3; 24/132 R; 132/137; 132/151; 132/153; 132/145; 132/277; 132/279

(58) Field of Classification Search
USPC .... 606/232, 72, 74; 24/132 R, 67.3; 132/137, 132/151, 153, 145, 277, 279
See application file for complete search history.

(56) References Cited

U.S. PATENT DOCUMENTS

| 1,426,111 A | 8/1922 | Sacker |
| 1,516,990 A | 11/1924 | Silverman |
| 1,847,347 A | 3/1932 | Maisto |
| 1,852,098 A | 4/1932 | Anderson |
| 2,075,508 A | 3/1937 | Davidson |
| 3,014,483 A | 12/1961 | McCarthy |

(Continued)

FOREIGN PATENT DOCUMENTS

| SU | 197801 | 6/1967 |
| WO | WO 95/21573 | 8/1995 |
| WO | WO 97/28745 | 8/1997 |

OTHER PUBLICATIONS

McCarthy, et al., "Tension (Stay) Suture Bridge", J. of International College of Surgeons, 34(5), pp. 613-614 (Nov. 1960).

(Continued)

*Primary Examiner* — Gary Jackson
*Assistant Examiner* — Diane Yabut
(74) *Attorney, Agent, or Firm* — Workman Nydegger; Randy Shen

(57) ABSTRACT

A suture clamp comprising a plurality of elements positioned together in a row, each element of the plurality of elements having a lower portion separated from an upper portion by a flexible neck, each element of the plurality of elements including a slot having an outwardly facing opening, the slots from the plurality of elements configured to accept a suture element through the row of elements and secure the suture element. A method of clamping a suture, including applying a biasing force to at least one element into the first position to provide access to the outwardly facing opening of the slot, passing the suture through a tissue layer, receiving the suture into the slot through the outward facing opening, and removing the biasing force to form a tortuous path between adjacently positioned elements of the plurality of elements.

20 Claims, 14 Drawing Sheets

U.S. PATENT DOCUMENTS

| | | | |
|---|---|---|---|
| 3,513,848 A | 5/1970 | Winston et al. | |
| 3,525,340 A | 8/1970 | Gilbert | |
| 3,664,345 A | 5/1972 | Dabbs et al. | |
| 3,732,719 A | 5/1973 | Pallotta | |
| 3,750,650 A | 8/1973 | Ruttgers | |
| 3,753,438 A | 8/1973 | Wood et al. | |
| 3,831,608 A | 8/1974 | Kletschka et al. | |
| 3,931,821 A | 1/1976 | Kletschka et al. | |
| 3,976,079 A | 8/1976 | Samuels et al. | |
| 4,287,489 A | 9/1981 | Pinkham | |
| 4,291,698 A | 9/1981 | Fuchs et al. | |
| 4,387,489 A | 6/1983 | Dudek | |
| 4,400,879 A | 8/1983 | Hildreth | |
| 4,505,274 A | 3/1985 | Speelman | |
| 4,577,635 A | 3/1986 | Meredith | |
| 4,644,956 A | 2/1987 | Morgenstern | |
| 4,667,675 A | 5/1987 | Davis | |
| 4,683,895 A | 8/1987 | Pohndorf | |
| 4,750,492 A | 6/1988 | Jacobs | |
| 4,773,421 A | 9/1988 | Davis | |
| 4,813,586 A | 3/1989 | Seifert | |
| 4,823,794 A | 4/1989 | Pierce | |
| 4,866,818 A | 9/1989 | Thompson | |
| 5,009,663 A | 4/1991 | Broomé | |
| 5,071,430 A | 12/1991 | de Salis et al. | |
| 5,078,731 A | 1/1992 | Hayhurst | |
| 5,158,566 A | 10/1992 | Pianetti | |
| 5,160,339 A | 11/1992 | Chen et al. | |
| 5,171,251 A | 12/1992 | Bregen et al. | |
| 5,176,682 A | 1/1993 | Chow | |
| 5,203,787 A | 4/1993 | Noblitt et al. | |
| 5,219,359 A | 6/1993 | McQuilkin et al. | |
| 5,234,449 A | 8/1993 | Bruker et al. | |
| 5,236,445 A | 8/1993 | Hayhurst et al. | |
| 5,258,015 A | 11/1993 | Li et al. | |
| 5,282,832 A | 2/1994 | Toso et al. | |
| 5,306,280 A | 4/1994 | Bregen et al. | |
| 5,330,442 A * | 7/1994 | Green et al. | 606/232 |
| 5,376,101 A | 12/1994 | Green et al. | |
| 5,383,905 A | 1/1995 | Golds et al. | |
| 5,391,173 A | 2/1995 | Wilk | |
| 5,409,499 A | 4/1995 | Yi | |
| 5,462,558 A | 10/1995 | Kolesa et al. | |
| 5,474,572 A | 12/1995 | Hayhurst | |
| 5,501,698 A | 3/1996 | Roth et al. | |
| 5,514,159 A | 5/1996 | Matula et al. | |
| 5,521,184 A | 5/1996 | Zimmerman | |
| 5,543,520 A | 8/1996 | Zimmerman | |
| 5,593,422 A | 1/1997 | Muijs Van der Moer et al. | |
| 5,593,425 A | 1/1997 | Bonutti et al. | |
| 5,611,986 A | 3/1997 | Datta et al. | |
| 5,618,306 A | 4/1997 | Roth et al. | |
| 5,630,824 A | 5/1997 | Hart | |
| 5,645,553 A | 7/1997 | Kolesa et al. | |
| 5,669,917 A | 9/1997 | Sauer et al. | |
| 5,681,351 A | 10/1997 | Jamiolkowski et al. | |
| 5,709,708 A | 1/1998 | Thal | |
| 5,720,765 A | 2/1998 | Thal | |
| 5,725,556 A | 3/1998 | Moser et al. | |
| 5,728,109 A | 3/1998 | Schulze et al. | |
| 5,735,875 A | 4/1998 | Bonutti et al. | |
| 5,735,877 A | 4/1998 | Pagedas | |
| 5,749,898 A | 5/1998 | Schulze et al. | |
| 5,769,862 A | 6/1998 | Kammerer et al. | |
| 5,776,150 A | 7/1998 | Nolan et al. | |
| 5,782,864 A | 7/1998 | Lizardi | |
| 5,810,877 A | 9/1998 | Roth et al. | |
| 5,814,069 A | 9/1998 | Schulze et al. | |
| 5,846,254 A | 12/1998 | Schulze et al. | |
| 5,871,490 A | 2/1999 | Schulze et al. | |
| 5,893,592 A | 4/1999 | Schulze et al. | |
| 5,919,208 A | 7/1999 | Valenti | |
| 5,976,159 A | 11/1999 | Bolduc et al. | |
| 6,024,758 A | 2/2000 | Thal | |
| 6,066,160 A | 5/2000 | Colvin et al. | |
| 6,074,409 A | 6/2000 | Goldfarb | |
| 6,086,608 A | 7/2000 | Ek et al. | |
| 6,092,561 A | 7/2000 | Schmid | |
| 6,099,553 A | 8/2000 | Hart et al. | |
| 6,106,545 A | 8/2000 | Egan | |
| 6,126,677 A | 10/2000 | Ganaja et al. | |
| 6,143,017 A | 11/2000 | Thal | |
| 6,152,934 A | 11/2000 | Harper et al. | |
| 6,159,234 A | 12/2000 | Bonutti et al. | |
| 6,165,204 A | 12/2000 | Levinson et al. | |
| 6,174,324 B1 | 1/2001 | Egan et al. | |
| 6,200,329 B1 | 3/2001 | Fung et al. | |
| 6,203,565 B1 | 3/2001 | Bonutti et al. | |
| 6,231,592 B1 | 5/2001 | Bonutti et al. | |
| 6,254,615 B1 | 7/2001 | Bolduc et al. | |
| 7,033,379 B2 | 4/2006 | Peterson | |
| 7,108,710 B2 | 9/2006 | Anderson | |
| 7,806,910 B2 * | 10/2010 | Anderson | 606/232 |
| 2003/0167062 A1 * | 9/2003 | Gambale et al. | 606/138 |

OTHER PUBLICATIONS

U.S. Appl. No. 10/305,923, Nov. 1, 2004, Office Action.
U.S. Appl. No. 10/305,923, Mar. 3, 2005, Notice of Allowance.
U.S. Appl. No. 11/461,323, May 2, 2007, Office Action.
U.S. Appl. No. 11/461,323, Oct. 29, 2007, Office Action.
U.S. Appl. No. 11/461,323, Apr. 25, 2008, Office Action.
U.S. Appl. No. 11/461,323, Nov. 6, 2008, Office Action.
U.S. Appl. No. 11/461,323, Jul. 27, 2009, Office Action.
U.S. Appl. No. 11/461,323, Apr. 5, 2010, Notice of Allowance.
U.S. Appl. No. 11/461,323, Sep. 15, 2010, Issue Notification.

* cited by examiner

MULTI ELEMENT BIASED SUTURE CLIP

CROSS-REFERENCE TO RELATED APPLICATIONS

This is a continuation application of U.S. patent application Ser. No. 11/461,323, filed Jul. 31, 2006, and entitled "Multi Element Biased Suture Clip", now U.S. Pat. No. 7,806,910, which is a continuation application of U.S. patent application Ser. No. 10/305,923, filed Nov. 26, 2002, and entitled "Multi Element Biased Suture Clip", now U.S. Pat. No. 7,108,710, the disclosures of which are incorporated herein by this reference.

BACKGROUND OF THE INVENTION

1. The Field of the Invention

The present invention relates to systems for securing a pair of suture lengths together or for using a single strand of suture to secure tissues together at an operative site in a patient without necessarily tying a knot.

2. The Relevant Technology

Sutures are used to sew tissue together, and thereby close tissue openings, cuts or incisions during or after any of a very wide variety of medical procedures. Typically, the surgeon manually ties together a suture pair to close the opening; however, automatic suture tying systems have also been developed.

There are a number of disadvantages of knotting sutures together to secure tissues to one another. For example, manual knot tying requires considerable dexterity. Also, manual knot tying can take considerable time. Knot tying is further complicated by the fact that surgical sutures have low friction surfaces. Therefore, it is typically necessary for a surgeon to include many "throws" when tying the knot. This multiple-throw problem occurs even if an automatic knot tying device is used. Unfortunately, as the number of loops or "throws" incorporated into the knot increase, the knot becomes increasingly large and bulky. Moreover, the surgeon typically needs to handle strands of adequate suture length prior to commencing manual knot tying. Thus, manual knot tying requires considerable space both in which to view, and to perform, the actual suture knot tying. Therefore, knot tying is particularly difficult in areas of limited available space or access, such as, for example, at the back of the patient's heart during a coronary artery bypass graft (CABG) operation, or at the artery in the tissue tract after a femoral artery catheterization procedure. Manually tied knots often lock prior to reaching the intended amount of tension to be applied to the tissue. Furthermore, tissues are typically secured together by a pair of sutures wherein each of the sutures in the pair pass through both of the tissues which are then secured together by tying off the suture pair. It would instead be advantageous to provide a system which is adapted to secure tissue with suture, but without necessarily tying a knot.

BRIEF SUMMARY OF THE INVENTION

Embodiments of the present invention provide a suture clamping system. The present suture clamping system can be used to clamp a suture pair, or to use a single strand of suture to secure tissues together. In one embodiment, a plurality of elements define a slot sized to accept a suture element through the row of elements when at least one of the elements is in a first position, and wherein a tortuous path is formed through the row of elements when at least one of the elements is in a second position.

In various embodiments, the slot is generally parallel to the length of the row. In various embodiments, the at least one of the elements is a flexible element which is in the second position when not biased, and which moves into the first position when biased. In various embodiments, the direction in which the flexible element is biased is generally transverse to the length of the row.

In various embodiments, the present invention comprises a plurality of adjacent flexible elements connected together in a row. The elements are biased to first positions which define an opening slot along the row of elements. A tortuous path is formed through the elements when the elements are not biased.

Still other embodiments may also include a biasing/positioning device which is used to bias and hold the row of elements in the first position (at which time an opening is defined along the top of the row for receipt of the suture length or suture pair therein). Preferably, the biasing device is slidably received around the row of elements such that as the biasing force is removed, (e.g.: as the row of elements are slidably pushed or otherwise advanced through the biasing device), the elements then move to a non-biased position (at which time a tortuous path is formed along through the row of elements). Thus, a suture pair can effectively be clamped or "fastened" together when the sutures are held in such a tortuous path. Features of the present invention allow a physician to completely avoid manual suture knot tying. Therefore, the bulky multiple loops or "throws" required when knot tying can be minimized or eliminated. Instead, the suture pair is simply "clamped" or held together between the flexible elements.

Alternatively, the present system can be clamped onto a single suture and can thus act as an anchor preventing movement of a tissue layer along a single suture strand. Specifically, when using only a single strand of suture, the suture is clamped so that it does not move with respect to the clamping system.

DETAILED DESCRIPTION

In accordance with the present invention, a suture clamping system is provided. In preferred aspects, the suture clamping system comprises a plurality of individual flexible elements positioned together in a row. In various preferred embodiments, the individual flexible elements are shaped the same. Optionally, the row of elements is formed by positioning successive identically shaped elements adjacent to one another. It is to be understood, however, that the individual elements in the row need not be identical in shape to one another. It is also to be understood that the individual elements need not be positioned in direct "touching" contact side-by-side with one another, but may instead be positioned some distance apart from one another. As will also be explained, various embodiments of the invention may include rows of elements including both flexible and non-flexible elements. In fact, in one embodiment, only one flexible element is required.

One or more of these elements are preferably biased in a direction transverse to the length of the row. When biased, one or more flexible elements move to a first position at which the elements define a slot along the length of the row. The slot is specifically sized to receive a suture therein. When not biased, the one or more flexible elements return to a second (non-biased) position. When in a non-biased position, the elements form a tortuous path for the suture received therein.

Figure 5:
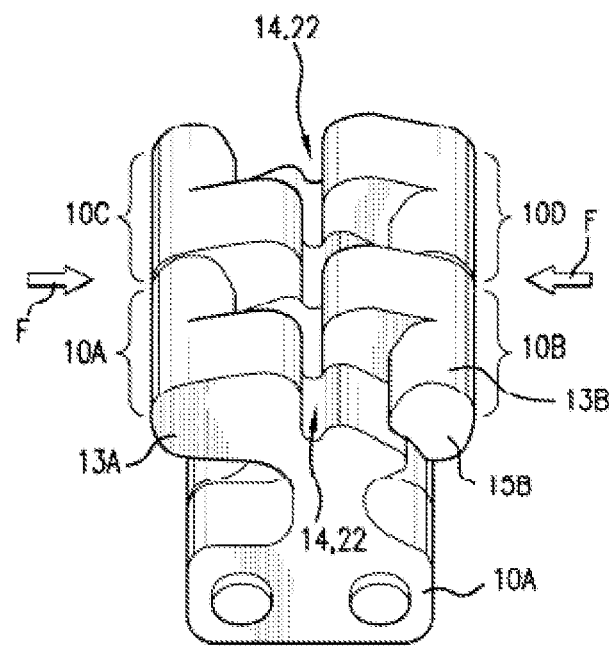
FIG. 5 is a perspective end view of the row of flexible elements as illustrated in FIG. 4.
Figure 6:
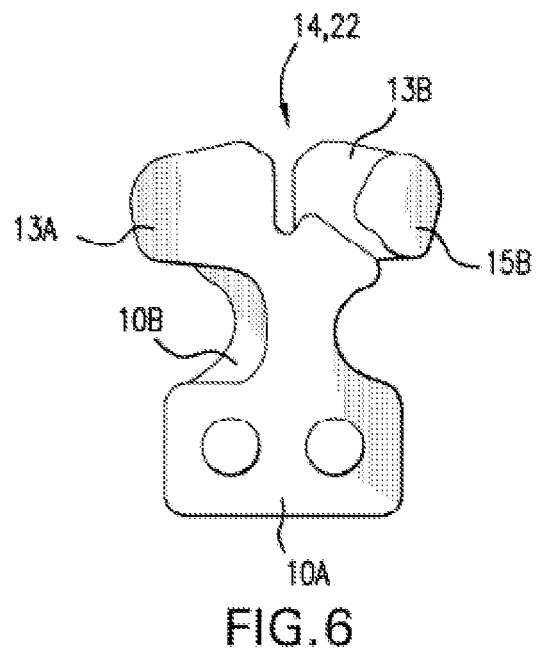
FIG. 6 is an end elevation view of the row of flexible elements as illustrated in FIGS. 4 and 5.
Figure 7:
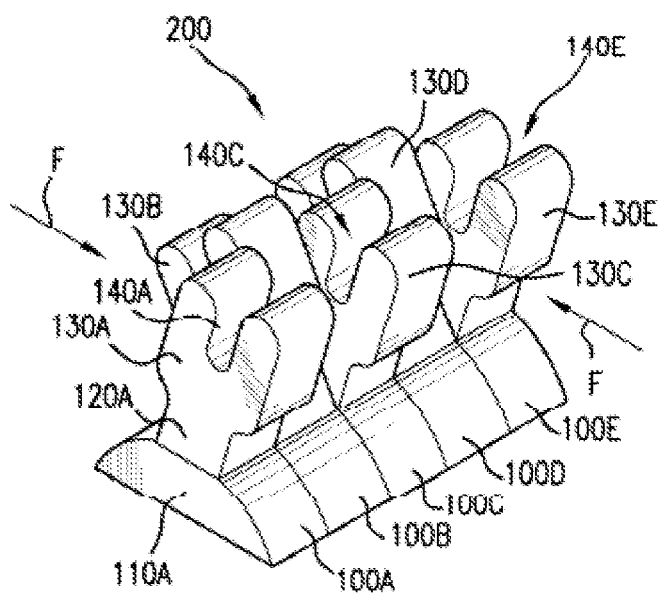
FIG. 7 is a perspective view of an alternate design of a row of flexible elements, with the elements in a non-biased position, forming a tortuous path therethrough.
Figure 8:
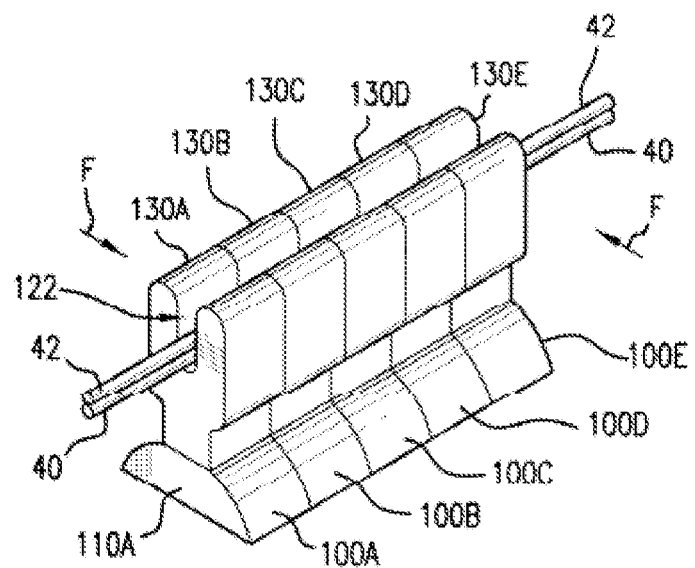
FIG. 8 is a perspective view of the row of elements of FIG. 7, with the elements biased into a first position such that an opening slot forms along the top of the row.
Figure 13:
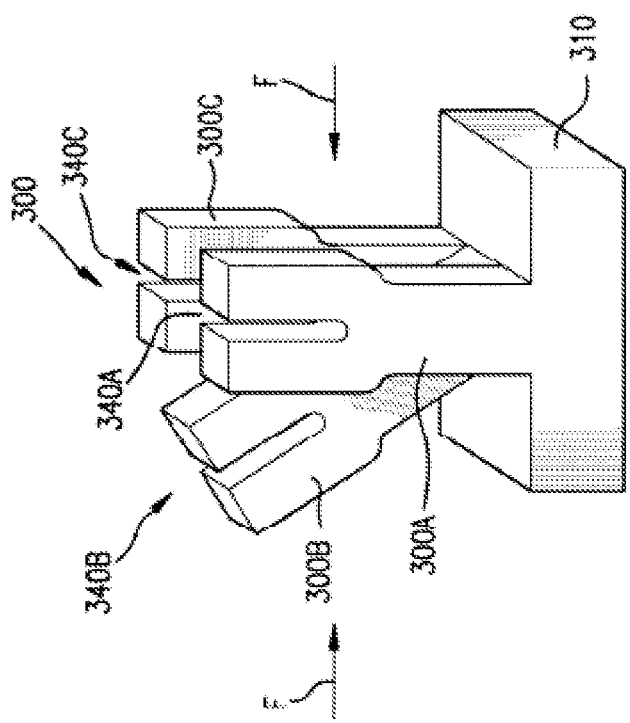
FIG. 13 is an exploded perspective view of an embodiment of the invention having two non-flexible elements with a single flexible element positioned therebetween.

FIGS. 1 to 6 illustrate a first preferred embodiment of the present invention, and FIGS. 7 and 8 illustrate a second preferred embodiment of the present invention. FIGS. 9 to 12 illustrate an exemplary positioning/biasing device for use with various embodiments of a suture clamp. FIG. 13 illustrates an embodiment of the invention having only one flexible element. FIGS. 14 to 18B show component parts of an embodiment of the device having a suture guide assembly, a pair of flexible suture capture elements, and a rail guide. FIGS. 19 to 22 show sequential steps in the deployment of the embodiment of the device shown FIGS. 14 to 18B.

Figure 1:
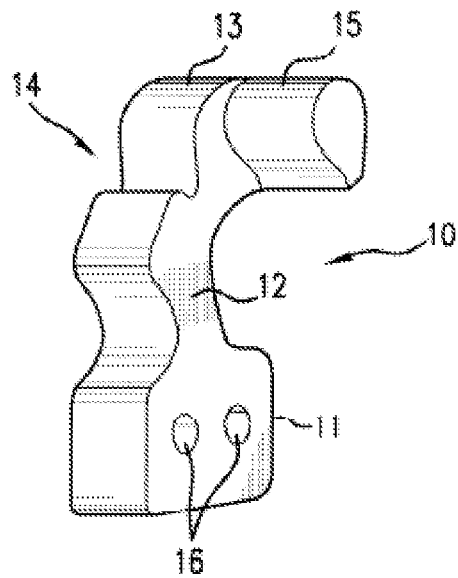
FIG. 1 is a perspective view of a single flexible element.

FIG. 1 illustrates an embodiment of a single clamping element 10. Element 10 has a lower portion 11, a neck 12, and an upper portion 13. A slot 14 is defined by upper portion 13. Also, an optional projection 15 extends longitudinally from upper portion 13. As will be explained, projections 15 provide contact surfaces between adjacent elements such that the elements may rest against one another when in a non-biased (second) position. It is to be understood that projections 15 are optional and that various embodiments of the present invention do not require projections 15 to operate.

Element 10 is preferably fabricated from a unitary block of Nitinol or other suitable flexible or elastic material, including various plastics and metals. Photochemical machining or other known techniques may be used to form element 10. Most preferably, each element 10 will be dimensioned to about 1 mm in height.

Figure 3:
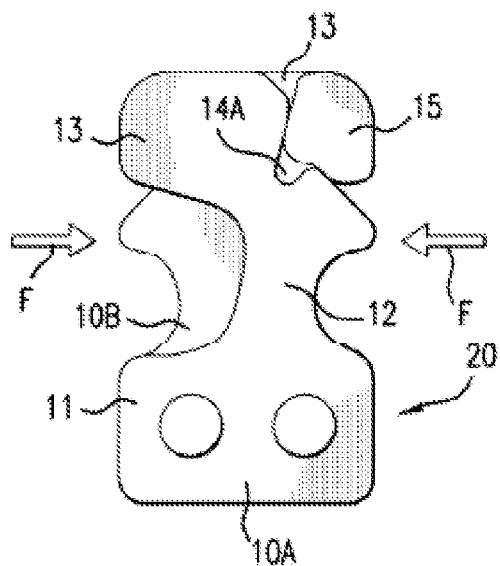
FIG. 3 is an end view of the row of flexible elements as illustrated in FIG. 2.
Figure 2:
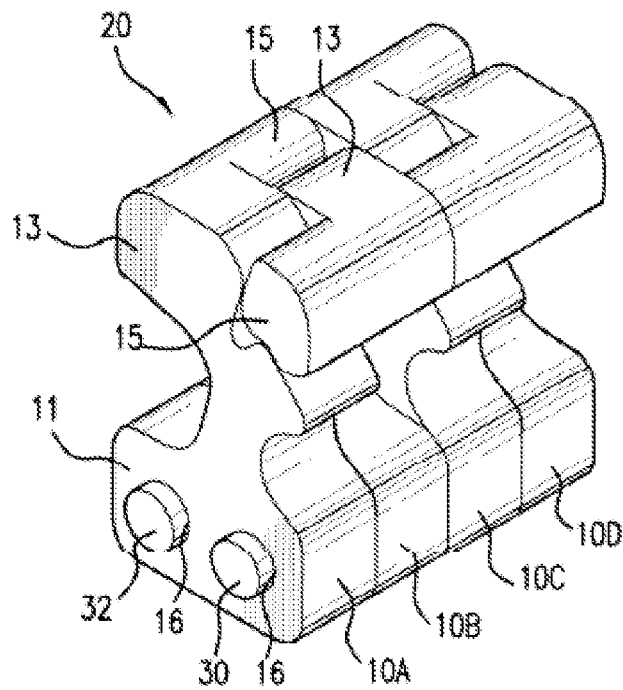
FIG. 2 is a perspective view of row of flexible elements as individually illustrated in FIG. 1, with the elements in a non-biased position, forming a tortuous path therethrough.

As can be seen in FIGS. 2 and 3, a plurality of flexible elements 10 (i.e.: 10A, 10B, 10C, 10D, etc.) can be positioned side-by-side forming row 20. Preferably, lower portions 11 of the successive elements 10 are positioned adjacent to one another such that their projections 15 interlock with upper portions 13 of adjacent elements (as shown in FIG. 2). Lower portions 11 of the successive elements 10 may optionally be connected together (side-by-side) by a variety of techniques, including fusion bonding and adhesives. Alternatively, lower portions 11 of the successive elements 10 may optionally be spaced some distance apart from one another (not shown).

In another embodiment, elements 10 may each optionally comprise a pair of holes 16 (see FIG. 1) such that elements 10A, 10B, 10C, 10D, can be positioned on rods 30 and 32, or a similar mounting element or structure.

In accordance with the present invention, a biasing force ("F" in FIG. 3) is applied to the upper portions of each of elements 10. Biasing force F is applied in a direction generally transverse to the length of the row. Thus, as can be seen, force F will squeeze row 20 from its sides. The bottom portions 11 of each of elements 10 are held in a constant position with respect to one another. Alternatively, an embodiment of the present invention may include a single unitary bottom portion (as opposed to the illustrated plurality of separate bottom portions 11). Thus, the device which comprises the row of elements can be machined or molded out of a solid block of material such that the elements have a common bottom portion (for example, as illustrated in FIG. 13). Having a thin neck 12, the upper portions 13 of each of elements 10 will tend to move apart in a direction transverse to the row of elements as biasing force F is applied.

Figure 4:
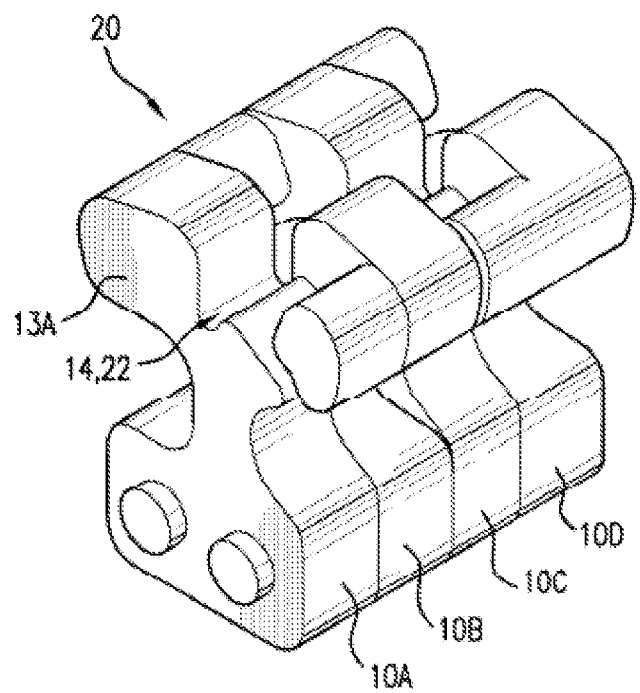
FIG. 4 is a perspective view of row of flexible elements as individually illustrated in FIG. 1, with the elements biased into a first position such that an opening slot forms along the top of the row.

As shown in FIGS. 4 to 6, when a sufficiently strong biasing force F is applied, elements 10 move to a first position in which a slot 22 forms along the top of row 20. (i.e. when adjacent slot defining features 14 in successive elements 10 are in alignment). At this time a pair of sutures 40 and 42 (see FIG. 10) can be positioned within slot 22. When force F is removed, elements 10 will naturally tend to return to their non-biased (or possibly biased against one another) position, at which time an upper portion 13A of a first element (10A) will abut against projection 15B of upper portion 13B of a second element (10B), as shown in FIGS. 2 and 3.

The flexible elements which are used to form the suture clamping device can be made in a variety of different shapes. For example, referring to FIGS. 7 and 8, a row 200 of flexible elements 100A, 100B, 100C, 100D, 100E, etc. are used to form a suture clamping device. Specifically, as shown in the non-biased position (i.e. FIG. 7), elements 100 each have a lower portion 110, a neck 120 and an upper portion 130. Upper portion 130 has a slot defining features 140 formed therein. As can be seen, element 110 is formed such that its neck 120 holds upper portion 130 (and slot defining features 140) at an angle when in the non-biased (FIG. 7) position.

Thus, when a squeezing force F is applied against flexible elements 100 on either side of row 200, elements will be biased into the position shown in FIG. 8 wherein the slot-defining features 140 of successive elements are positioned in alignment with one another to form a slot 122. A pair of sutures 40 and 42 can then be placed into slot 122. When the biasing force F is released, elements 110 will tend to move back to the position shown in FIG. 7, thus forming a tortuous path for sutures 40 and 42, passing therethrough.

In an alternate embodiment, the elements are formed such that a suture slot is instead formed when the elements are in their non-biased position. In such an embodiment, the application of a biasing force would move the elements into a position such that the tortuous suture path is formed therethrough. After the elements have been biased to move into positions forming the tortuous suture path therethrough, a clip or other fastening device can be used to hold the elements in the biased position, with the tortuous suture path passing therethrough.

Sutures 40 and 42 may preferably comprise opposite ends of a continuous suture loop which has been used to suture together an anastomosis graft or to close a hole in a blood vessel or other tissue wall, or to anchor one or more suture elements. Alternatively, sutures 40 and 42 may comprise ends of separate suture strands which are fastened (i.e. clamped) together by present invention.

Figure 9:
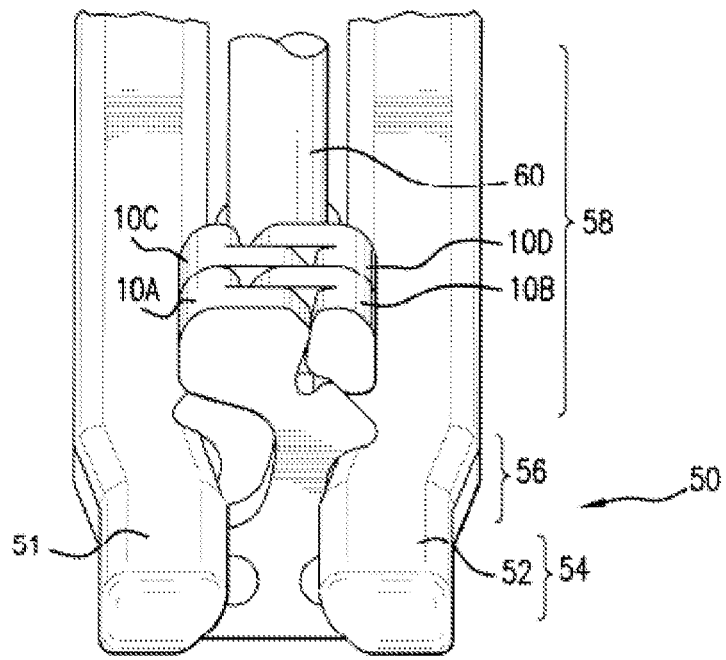
FIG. 9 is a perspective end view of a dual rail biasing device slidably received over the row of flexible elements, with the elements in a non-biased position, as shown in FIGS. 2 and 3.

In accordance with preferred aspects of the present invention, a method for clamping a suture pair is also provided. Preferably, this method includes biasing the row of adjacent flexible elements 10 (i.e.: applying force F) so that elements 10 move to the position (as shown in FIGS. 4 to 6) in which an opening slot 22 is formed therethrough. Preferably, this biasing force is applied in a direction transverse to the length of the row. Then, suture pair 40 and 42 is received into opening slot 22. Then, biasing force F is removed such that the adjacent flexible elements 10A, 10B, 10C, 10D, etc., move to positions which hold the suture pair in a tortuous path (as shown in FIGS. 2 and 3). Similarly, as seen in FIGS. 7 and 8, the present method may comprise: biasing the row of adjacent flexible elements 100 (i.e.: applying force F) so that elements 100 move to the first position (as shown in FIG. 9) in which an opening slot 122 is formed there along. Then, suture pair 40 and 42 is received into opening slot 122. Then, biasing force F is removed such that the adjacent flexible elements 100A, 100B, 100C, 100D, etc., move or spring back to positions which hold the suture pair in a tortuous path (as shown in FIG. 7).

The present method will be explained by reference to a dual rail positioning/biasing device shown in FIGS. 9 to 12, as follows.

A biasing device 50 may be provided as part of the present suture clamping system. In one embodiment, biasing device 50 comprises two rails 51 and 52 which are parallel to one another over two regions, and angled with respect to one another over another region. Specifically, as seen in FIG. 9, rails 51 and 52 are parallel with respect to one another in regions 54 and 58 and are angled with respect to one another in region 56. As also seen in FIG. 9, a push rod 60 is used to successively push elements 10A, 10B, 10C and 10D distally from region 58, and then through regions 56 and 54.

Figure 10:
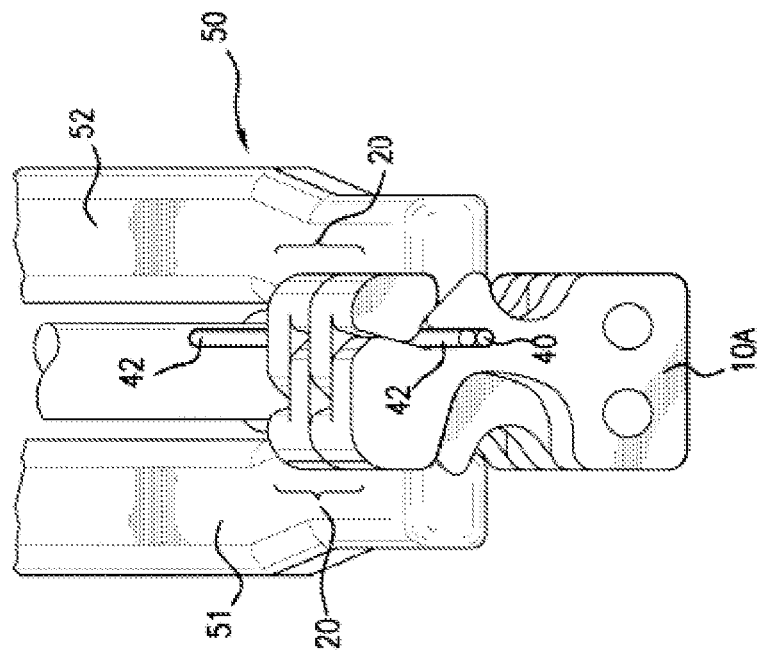
FIG. 10 is in a view similar to FIG. 9, but including as suture pair received in the slot formed through the row of elements.
Figure 11:
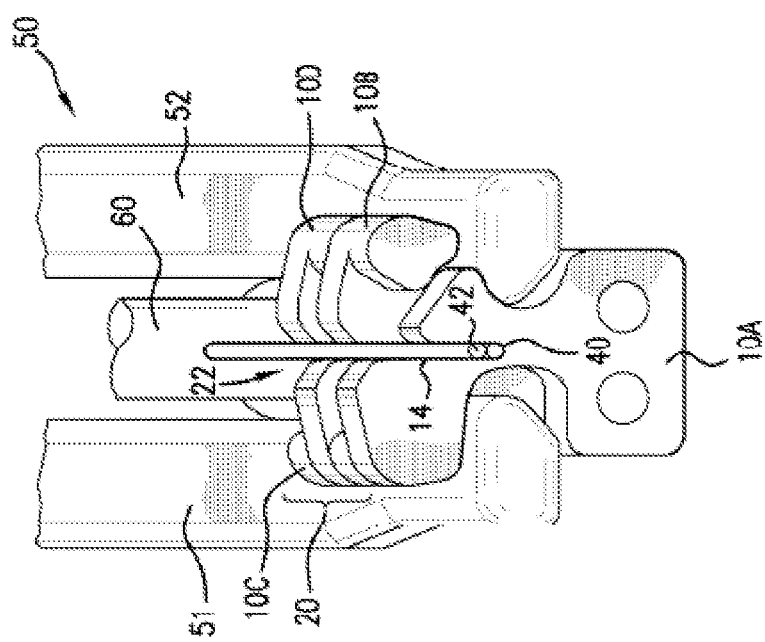
FIG. 11 is a perspective end view of the row of flexible elements after it has been pushed fully through the dual rail biasing device, such that the elements return to a non-biased position, trapping the suture pair in a tortuous path therein, as shown in FIGS. 2 and 3.
Figure 12:
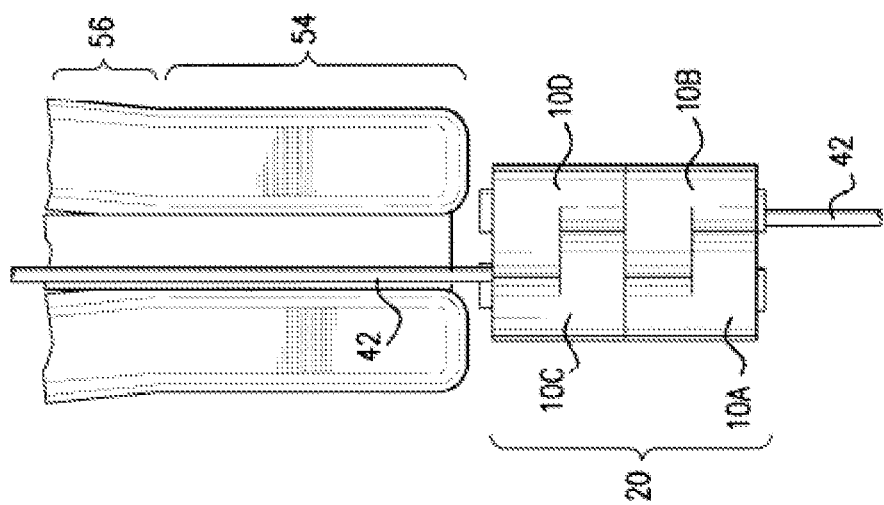
FIG. 12 is a top plan view corresponding to FIG. 11.
Figure 14:
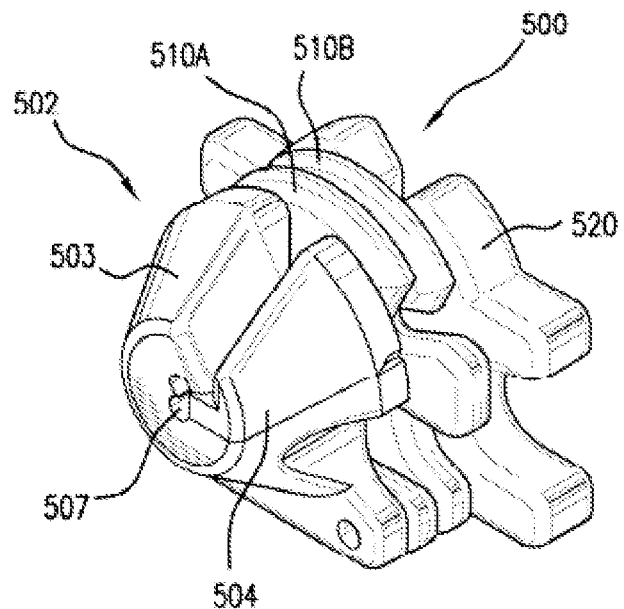
FIG. 14 is a perspective view of an embodiment of the invention further comprising a suture guide assembly, a pair of flexible suture capture elements and a rail guide.
Figure 15:
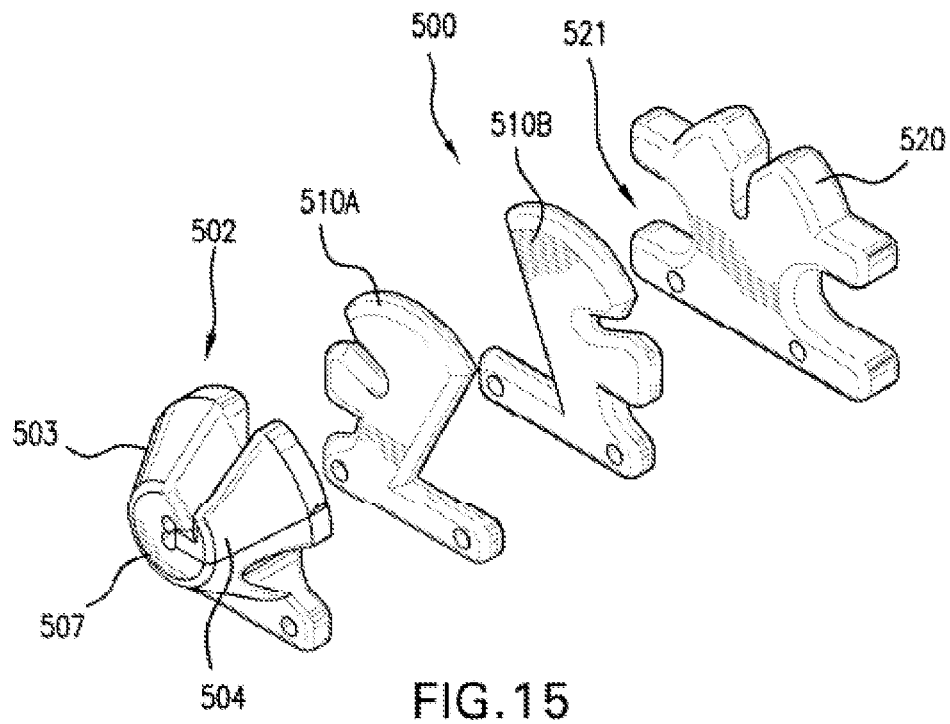
FIG. 15 is an exploded perspective view of the invention shown in FIG. 14.
Figure 16A:
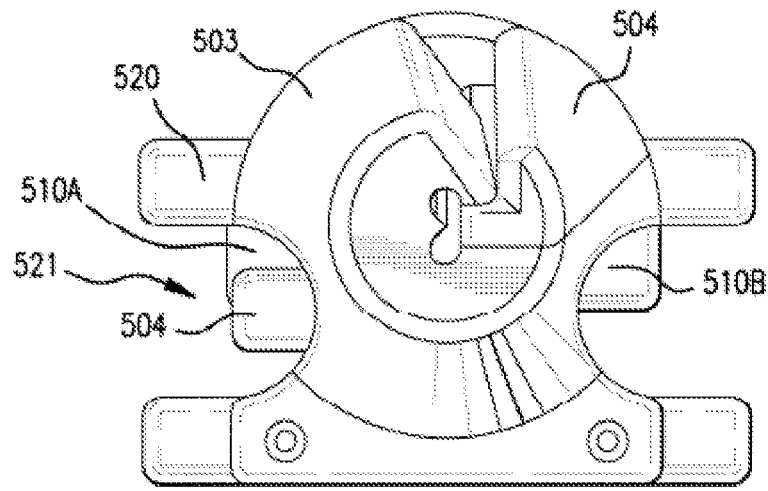
FIG. 16A is a front elevation view of the embodiment of the invention shown in FIG. 14 in a closed position.
Figure 16B:
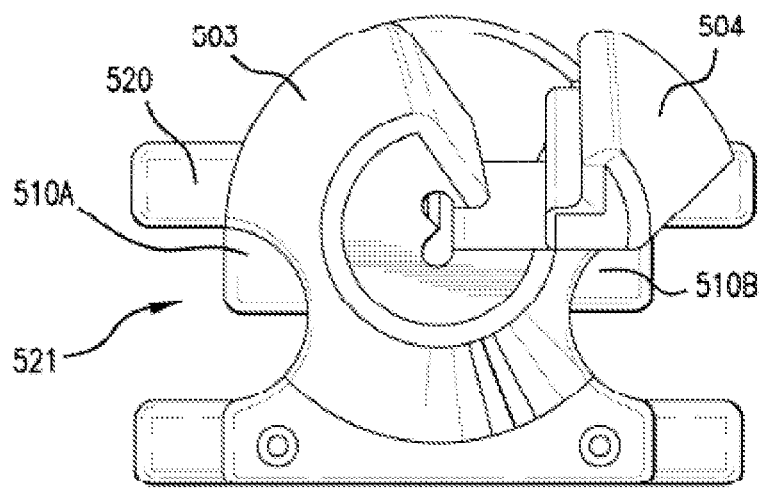
FIG. 16B is a front elevation view of the embodiment of the invention shown in FIG. 14 in an open position.
Figure 17A:
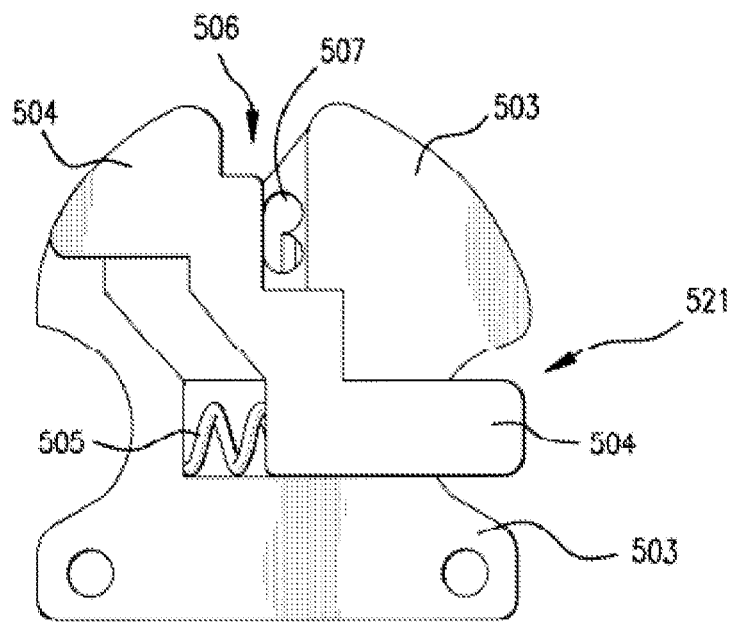
FIG. 17A is a rear view of the suture guide assembly in a closed position (corresponding to FIG. 16A).
Figure 17B:
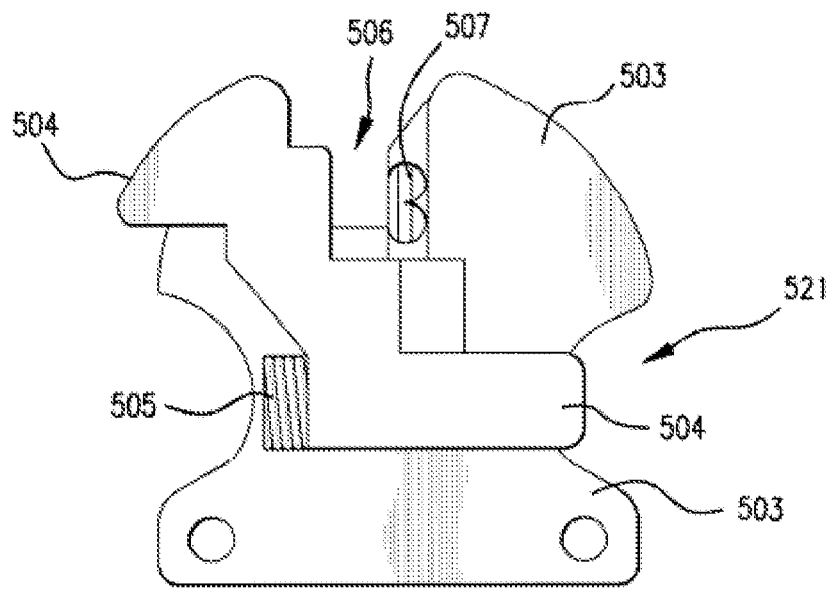
FIG. 17B is a rear view of the suture guide assembly in an open position (corresponding to FIG. 16B).

From the position shown in FIG. 9, push rod 60 is advanced such that row 20 of elements 10 is pushed into region 54 (as shown in FIG. 10) wherein rails 51 and 52 are positioned closer together, such that individual slot defining features 14 are put into alignment (forming slot 22 along the length of row 20). As shown in FIG. 10, a suture pair 40, 42 can then be positioned within slot 22. Lastly, as shown in FIGS. 11 and 12, row 20 is pushed out of the distal end of biasing device 50. As shown in FIG. 12, the biasing force on the sides of row 20 is removed such that elements 10A, 10B, 10C and 10D return to their non-biased position, thus forming a tortuous path for suture pair 40 and 42 passing therethrough.

As stated above, the present invention may comprise a plurality of flexible elements. It is to be understood, however, that embodiments of the invention may also comprise non-flexible elements, or various combinations of flexible and non-flexible elements. For example, as shown in FIG. 13, a row 300 of elements (which may optionally have a single unitary base 310) may have a single flexible element 300B disposed between (or otherwise adjacent to) non-flexible elements 300A and 300C. When a biasing force F is applied to the sides of the device, flexible element 300B will move to a position such that elements 300A, 300B and 300C will be placed in alignment. Then, a suture, or suture pair can easily be threaded through opening slots 340A, 340B and 340C. When biasing force F is removed, element 300B will tend to spring back into the position shown in FIG. 13, thereby forming a tortuous path, firmly holding the suture(s) therein.

FIGS. 14 to 18B show an alternate embodiment of the present invention that includes a suture clamp assembly 500 including a suture guide assembly 502, a pair of flexible elements 510A and 510B and a rail guide 520. Suture guide assembly 502 includes a suture guide 503 and a suture lock 504. As can be seen in FIGS. 16A to 17B, suture lock 504 is movable with respect to suture guide 503, thus permitting a suture or suture pair to be inserted therebetween, and then clamped, as follows. As shown in FIGS. 16A and 17B, suture lock 504 is initially position adjacent to suture guide 503 (by the action of spring 505). When using the device, the end of suture lock 504 which extends in to cavity 521 in rail guide 520 is pushed. Such force compresses spring 505 so that suture lock 504 moves to the position shown in FIGS. 16B and 17B, thereby opening passageway 506, permitting a suture, or suture pair to be inserted therein. Thereafter, the force can be removed from the end of suture lock 504 which extends in to cavity 521 such that, spring 505 expands and suture lock 504 returns to the position shown in FIGS. 16A and 17A, thereby trapping a suture or suture pair in passageway 506.

Figure 18A:
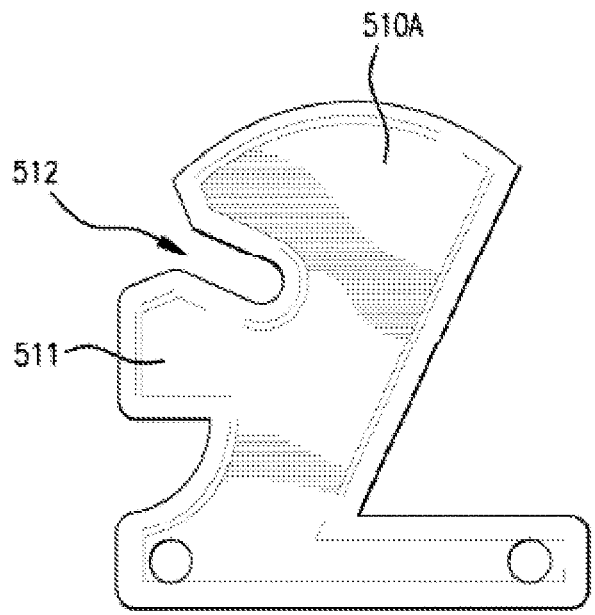
FIG. 18A is a front view of a pair of suture capture elements in a non-biased position.

Behind suture guide assembly 502 are positioned one or more flexible elements which are used to capture a suture or suture pair. These flexible elements operate in the same manner as the "row of flexible elements" described with regard to other embodiments herein. Specifically, flexible elements 510A and 510B have a non-biased position as shown in FIG. 18A. When a biasing force is applied to the underside of projections 511, flexible elements 510A and 510B move to the positions shown in FIG. 18B, at which time their slots 512 move into alignment with one another. When slots 512 of flexible elements 510A and 510B are positioned in alignment, a suture or suture pair can be received therein. Then, the biasing forces can be removed from projections 511, causing the flexible elements to move towards the position shown in FIG. 18A, thereby forming a tortuous path for a suture passing therethrough. It is to be understood that the present invention encompasses embodiments with more than two flexible suture capture elements 510, or even as few as one flexible and one non-flexible element.

In optional preferred aspects, both the suture guide 503 and the suture lock 504 are dimensioned such that the opening slot 507 (formed in passageway 506 in which the suture(s) are trapped) is not co-linear with the opening slots 512 through flexible elements 510A and 510B. An advantage of opening slot 507 not being co-linear with the path through opening slots 512 is that this further adds to the tortuosity of the suture path through the device, and permits more exact positioning of the device with respect to the target tissue.

Figure 18B:
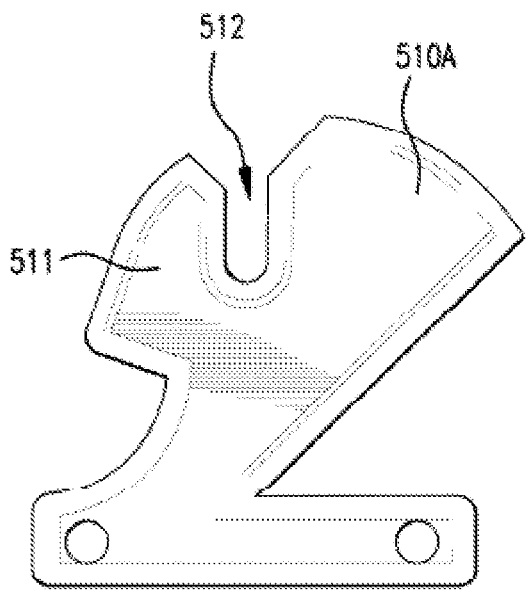
FIG. 18B is a front view of a pair of suture capture elements in a biased position, thus forming a suture opening therethrough.
Figure 19:
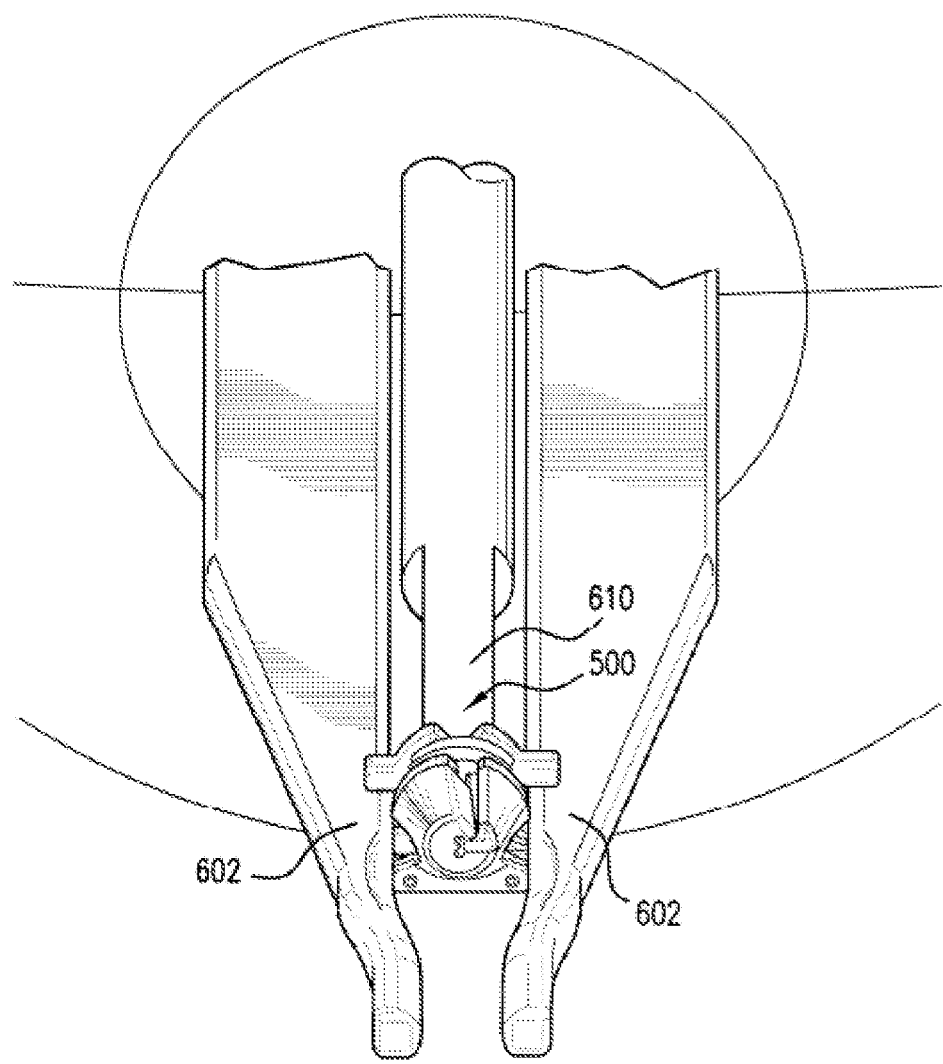
FIG. 19 is a top perspective view of the device of FIG. 14, positioned on a pair of rails prior to deployment.
Figure 20:
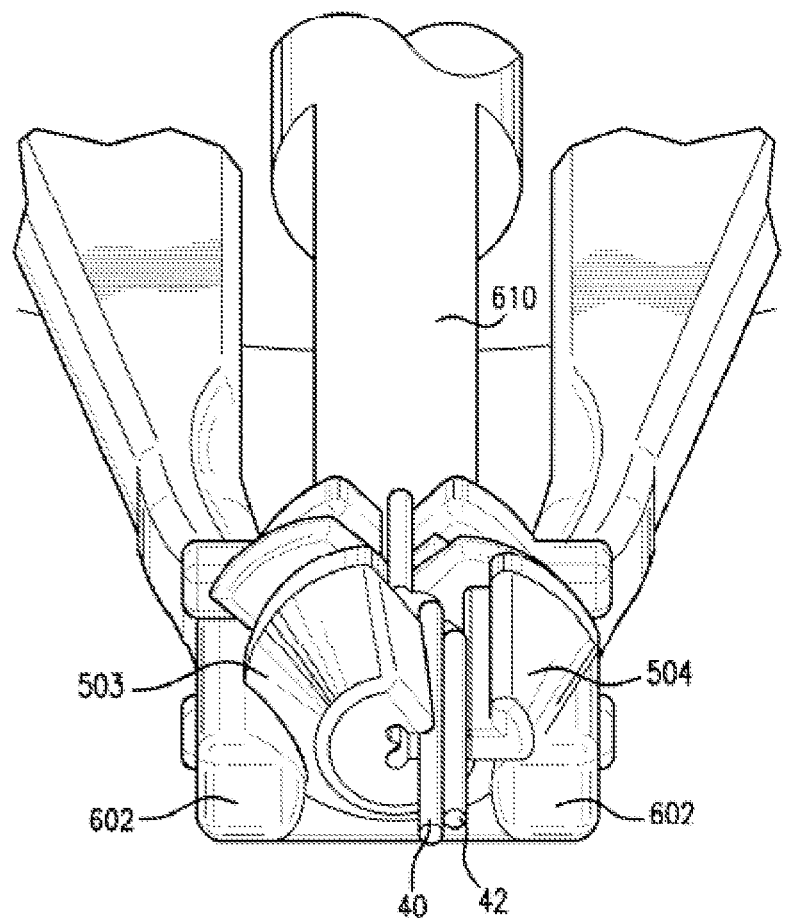
FIG. 20 is a view similar to FIG. 19, but with the device advanced to a position such that the rails cause the device to open to receive a suture pair therein.
Figure 21:
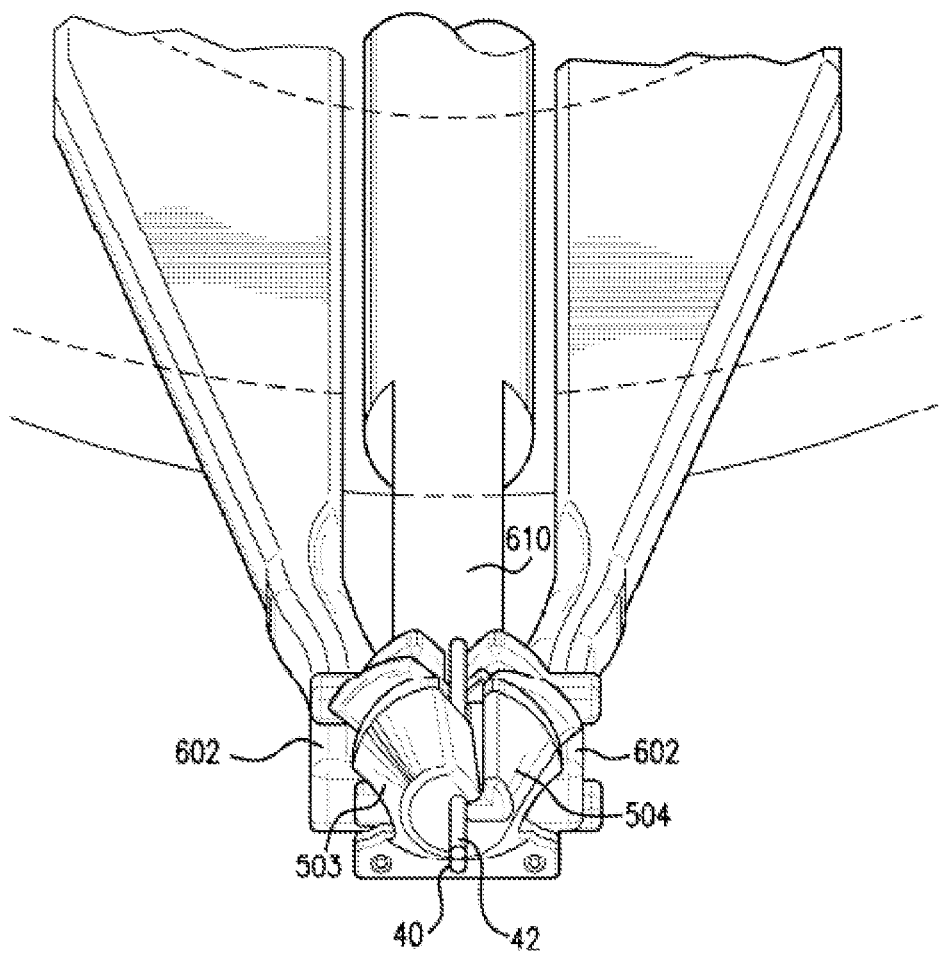
FIG. 21 is a view similar to FIG. 20, but with the device advanced to a position such that the suture guide assembly projects beyond the distal ends of the rails, showing the suture guide assembly locking onto the suture pair.
Figure 22:
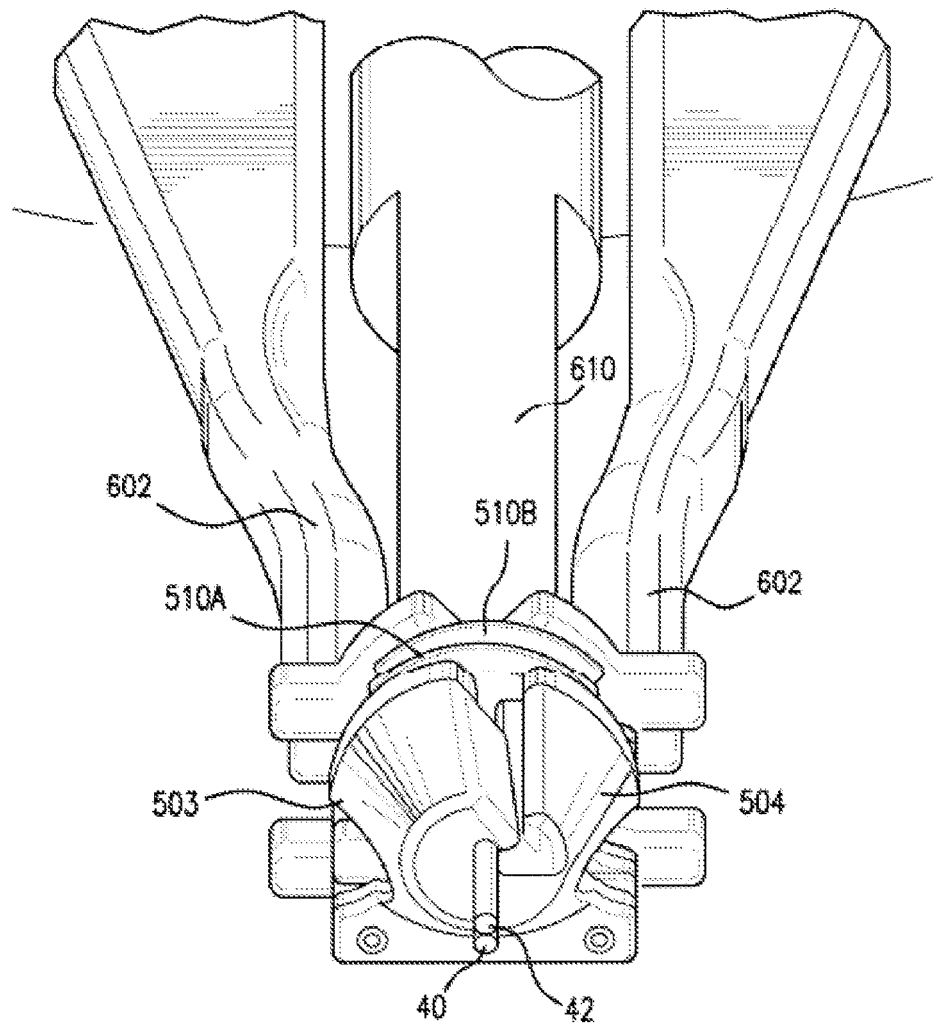
FIG. 22 is a view similar to FIG. 21, but with the entire device advanced beyond the distal ends of the pair of rails, showing the suture capture elements locking onto the suture pair.

FIGS. 19 to 22 show the deployment of the embodiment of the invention shown in FIGS. 14 to 18B, as follows. As shown in FIG. 19, suture clamp assembly 500 is initially positioned between rails 602, with a push rod 610 abutting against the rear of rail guide 520. Next, push rod 610 is used to advance the suture clamp assembly 500 to the position shown in FIG. 20 where the spacing between rails 602 narrows. Thus, one of the rails 602 will push on the end of suture lock 504 in cavity 512 so that suture lock 504 moves apart from suture guide 503, as explained above. In addition, advancing flexible elements 510A and 510B to the region where the spacing of rails 602 narrows will move flexible elements 510A and 510B to their biased position (FIG. 18B). At this time, a pair of sutures 40 and 42 can be received therein. Next, push rod 610 is used to advance the suture clamp assembly 500 to the position shown in FIG. 21 where suture guide assembly 502 is advanced beyond the distal end of the rails 602. Accordingly, suture lock 504 moves back into position against suture guide 503, thereby trapping sutures 40 and 42 therebetween. Lastly, as shown in FIG. 22, push rod 610 is used to fully push assembly 500 out beyond the distal end of rails 602. At this time, flexible elements 510A and 510B spring back to their non-biased positions, thus forming a tortuous path for sutures 40 and 42 passing therethrough. Accordingly, the row of flexible elements 510A and 510B assist suture guide assembly 502 in clamping onto sutures 40 and 42, thereby operating as a system which fastens the sutures together. In accordance with this embodiment of the invention, the suture guide assembly 502 fastens onto the suture (or suture pair) prior to flexible elements 510A and 510B fastening onto the suture(s). The suture guide assembly 502 can be positioned immediately adjacent to the tissue target site, if desired. After the suture guide assembly 502 has clamped onto the suture(s), the flexible elements 510A and 510B will sequentially clamp onto the suture(s), thereby taking up any slack in the suture(s) from the proximal side of the device. In other words, as each of the elements in the row of flexible elements is sequentially pushed out from between rails 602, the flexible elements will sequentially move to their non-biased positions, drawing in suture through rail guide 520. Since the suture is pulled in from the rail guide (i.e. the proximal) end of the device, it will not pull on the suture(s) from the suture guide assembly (i.e. the distal) end of the device. This minimizes inadvertent pulling on the sutures at the target tissue location (i.e. at the distal) end of the device).

The present system can be positioned directly adjacent to the operative site at which it is desirable to secure the suture pair. Specifically, the present system can be deployed without pulling suture at the surgical site as the suture pair is secured together. Rather, in preferred embodiments, as the present system is deployed, it pulls in suture from end of the clamp positioned away from the operative site. In contrast, manual or even automatic knot tying systems may either result in a loose knot being positioned at a small distance away from the operative site, or an overly tight knot pulling excessively on the tissues.

In addition, the present system can minimize the extent to which suture at the surgical site is pulled as it secures the suture(s). As the present system is deployed, it simply tightens together a suture pair at the operative site. In contrast, when tying together a suture pair, it is typically difficult to tie a knot very close to the operative site without excessively pulling on the tissues being tied together.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture clamp comprising a plurality of elements positioned together in a row, each element of the plurality of elements having a lower portion and an upper portion, the plurality of elements defining a slot sized to accept a suture element through the row of elements when at least one of the elements is in a first position and secure the suture element within the slot in a second position, adjacently positioned upper portions of the elements of the plurality of elements being at least partially overlapping in threes axes of the row and in an alternating orientation one to another along a longitudinal length of the row without the suture element disposed within the slot.

2. The suture clamp according to claim 1, wherein each element of the plurality of elements has the same configuration.

3. The suture clamp according to claim 1, further comprising a flexible neck disposed between the upper portion and the lower portion.

4. The suture clamp according to claim 1, wherein the slot is configured to receive a second suture element.

5. The suture clamp according to claim 1, wherein pairs of said plurality of elements are orientated in the same direction longitudinally along the row of elements.

6. A suture clamp comprising a plurality of differently-formed elements positioned together in a row, each element of the plurality of elements having a lower portion separated from an upper portion by a flexible neck, each element of the plurality of elements including a slot having an outwardly facing opening, the slots from the plurality of differently-formed elements are configured to accept a suture element through the row of elements when at least one of the elements is in a first position and secure the suture element when at least one of the elements is in a second position, adjacently positioned upper portions of the elements of the plurality of elements being at least partially overlapping in threes axes of the row and in an alternating orientation one to another along a longitudinal length of the row without the suture element disposed within the slot.

7. The suture clamp according to claim 6, wherein the flexible element is in the first position when biased.

8. The suture clamp according to claim 6, wherein the suture clamp is constructed of shape memory material.

9. The suture clamp according to claim 6, wherein each said element of said plurality of elements is movable independently of the remainder of the plurality of elements.

10. The suture clamp according to claim 6, further comprising a suture guide disposed on one side of a pair of elements of the plurality of elements and a rail guide disposed on an opposite side of the pair of elements of the plurality of elements.

11. The suture clamp according to claim 10, wherein the suture guide further comprises a biased, slidable lock.

12. The suture clamp according to claim 10, wherein each of the suture guide and the rail guide includes an opening slot, the opening slot in each of the suture guide and the rail guide is not co-linear with the slots of the plurality of elements.

13. The suture clamp according to claim 12, wherein the opening slot of the suture guide is configured to receive two suture element portions.

14. A method of clamping a suture passing through a tissue layer with a suture clamp system comprising a plurality of elements positioned together in a row, each element of the plurality of elements having a lower portion separated from an upper portion by a flexible neck, each element of the plurality of elements including a slot having an outwardly facing opening, the slots from the plurality of elements are configured to accept a suture element through the row of elements when at least one of the elements is in a first position and secure the suture element when at least one of the elements is in a second position, adjacently positioned upper portions of the elements of the plurality of elements being at least partially overlapping in threes axes of the row and in an alternating orientation one to another along a longitudinal length of the row without the suture element being disposed within the slot, the method comprising:
  applying a biasing force to at least one element into the first position to provide access to the outwardly facing opening of the slot,
  passing the suture through a tissue layer,
  receiving the suture into the slot through the outward facing opening, and
  removing the biasing force to form a tortuous path between adjacently positioned elements of the plurality of elements as the at least one element moves from the first position to the second position.

15. The method according to claim 14, wherein applying the biasing force comprises using a biasing device to bias the at least one element and removing the biasing force comprises slidably advancing the row of elements through a biasing device.

16. The method according to claim 15, wherein the receiving step comprises receiving two sutures into the slot.

17. The method according to claim 14, wherein applying the biasing force comprises biasing in a direction transverse to a length of the row.

18. The method according to claim 14, further comprising displacing a suture lock from a first lock position to a second lock position displaced from the first lock position and transverse to the at least one element.

19. The method according to claim 18, wherein the suture lock is biased to return to the first lock position.

20. The method according to claim 14, further comprising securing the row of elements to the suture.

* * * * *